(12) United States Patent
Dupriez et al.

(10) Patent No.: US 6,872,538 B1
(45) Date of Patent: Mar. 29, 2005

(54) HIGH-THROUGHPUT SCREENING DIAGNOSTIC AND/OR DOSAGE METHOD OF AN AGONIST AND/OR AN ANTAGONIST FOR A CALCIUM-COUPLED RECEPTOR

(75) Inventors: Vincent Dupriez, Brussels (BE); Michel Detheux, Louvain-la-Neuve (BE); Marc Parmentier, Brussels (BE)

(73) Assignee: Euroscreen s.a. (BE)

( * ) Notice: Subject to any disclaimer, the term of this patent is extended or adjusted under 35 U.S.C. 154(b) by 0 days.

(21) Appl. No.: 09/743,405

(22) PCT Filed: Jul. 6, 1999

(86) PCT No.: PCT/BE99/00087

§ 371 (c)(1),
(2), (4) Date: Mar. 13, 2001

(87) PCT Pub. No.: WO00/02045

PCT Pub. Date: Jan. 13, 2000

(30) Foreign Application Priority Data

Jul. 6, 1998 (EP) ............................................ 98870149

(51) Int. Cl.⁷ ...................... G01N 33/53; G01N 33/543; C07K 17/00
(52) U.S. Cl. ........................ 435/7.1; 435/7.2; 435/7.92; 530/350
(58) Field of Search ........................ 435/7.1, 7.2, 7.92, 435/7.23, 287.1, 28; 530/350

(56) References Cited

U.S. PATENT DOCUMENTS 5,422,266 A  6/1995  Cormier et al. .......... 435/252.3
5,714,666 A  2/1998  Pritchett et al. ................ 800/2

FOREIGN PATENT DOCUMENTS

EP  0341477  4/1989  ........... C12N/15/00

OTHER PUBLICATIONS

Shimomura, et al, 1993, Biochem. J., 296: 549–551.*
Stables, et al, 1997, Anal. Biochem., 252: 115–126.*
Le Poul, et al, 2002, J. Biomolecular Screening, 7(1): 57–65.*
Knight, et al, 1993, J. Cell Biol., 121(1): 83–90.*
Saran, et al, 1994, FEBS Letters, 337: 43–47.*

* cited by examiner

Primary Examiner—Elizabeth Kemmerer
Assistant Examiner—Sandra Wegert
(74) Attorney, Agent, or Firm—Kathleen M. Williams; Palmer & Dodge LLP (57) ABSTRACT

The present invention is related to a diagnostic an/or dosage method of an agonist and/or an antagonist and/or a modulator for a calcium-coupled receptor and/or channel and/or any other calcium-coupled protein, comprising the following successive steps: disposing the agonist and/or the antagonist and/or the modulator upon a solid support; Incubating one or more cell(s) expressing apoaequorin and said calcium-coupled receptor with coelenterazine in order to reconstitute an active aequorin in said cell(s). The present invention is also related to the diagnostic and/or dosage device intended for the method according to the invention.

8 Claims, 6 Drawing Sheets

HIGH-THROUGHPUT SCREENING DIAGNOSTIC AND/OR DOSAGE METHOD OF AN AGONIST AND/OR AN ANTAGONIST FOR A CALCIUM-COUPLED RECEPTOR

This is the U.S. National Phase under U.S.C. §371 of International Patent Application PCT/BE99/00087, filed Jul. 6, 1999.

FIELD OF THE INVENTION

The present invention is related to a high-throughput screening diagnostic and/or dosage method and device of an agonist and/or an antagonist for a calcium-coupled receptor and the agonist and/or antagonist of said calcium-coupled receptor identified by said method and device.

BACKGROUND OF THE INVENTION AND STATE OF THE ART

A lot of G-protein-coupled receptors (GPCR) trigger, upon binding of an agonist, a transient increase in intracellular calcium concentration. This variation acts as an internal secondary messenger and is an important modulator of many physiological mechanisms (reviewed by Rink (1990), Tsunoda (1993) and by Santella & Carafoli (1997)). Measurement of intracellular calcium concentration in cells expressing a GPCR can thus be used to monitor the efficacy of activation of a GPCR by various compounds known —or suspected—to be a ligand for this GPCR.

The activation of other receptors such as ions channels may also induce an intracellular calcium concentration.

Changes in calcium concentration can be detected by several means and methods, like the use of fluorescent dyes (for example: fura-2, fluo-3, fluo-4 and indo-1).

However, $Ca^{++}$ sensitive dyes have limitations. Activation of the dyes with an excitation beam requires complicated and expensive instruments and limits the use of the plastic labware such as microtiter plates.

Another method for intracellular calcium concentration measurement is the use of cell lines overexpressing a GP and apoaequorin, such an described by Sheu et al. (1993). In this system, cells expressing apoaequorin are incubated with coelenterazine, which is the co-factor of aequorin. During this incubation, coelenterazine enters the cell and conjugates with apoaequorin to form aequorin, which is the active form of the enzyme. Upon incubation of the cells with an agonist of the GPCR, intracellular calcium concentration increases. This increase leads to the activation of the catalytic activity of aequorin, which oxidises coelenterazine and yields apoaequorin, coelenteramide, $CO_2$ and light. Once the photon has been emitted, the complex must dissociate and apoaequorin must recombine with a new coelenterazine molecule to be able to emit light again. Thus, in this system, measurement of light emission following agonist addition reflects its ability to activate the GPCR and thus to increase intracellular calcium concentration. Because light is emitted only during 20 to 30 seconds after; activation of the GPCR, recording of the emitted light must be performed during the few seconds following agonist addition to the cells. This flash-type signal is due to the fact that (1) intracellular calcium increase triggered by GPCR is only transient and (2) as mentioned earlier, after oxidation of coelenterazine, apoaequorin must recombine with coelenterazine to be able to emit light again.

The Patent Application EP-0341477 teaches the expression of jellyfish photoprotein aequorin in a mammalian cell system by cloning gene pAQ440 specifying the biosynthesis of the aequorin into an expression vector plasmid of a mammalian cell system, subjecting the resulting plasmid to transfection and producing the photoprotein aequorin in the mammalian cell.

The U.S. Pat. No. 5,422,266 describes a gene encoding apoaequorin protein included in a vector capable of expressing the apoaequorin in E. coli.

The U.S. Pat. No. 5,714,666 describes mammalian cell lines or transgenic animals expressing apoaequorin and a receptor involved in the modulation of intracellular calcium. This document also describes a method of measuring intracellular calcium comprising adding coelenterazine cofactors to said mammalian cells expressing apoaequorin and measuring photoemission where emission of photons is indicative of intracellular calcium concentration.

However, the methods of the state of the art require firstly the spreading of cells from a mammalian cell line expressing apoaequorin on a solid support (for example a 96-well plate), secondly the addition of the coelenterazine cofactor upon the cells and incubation to, reconstitute a functional aequorin, thirdly the preparation of the agent affecting a receptor involved in the modulation of intracellular calcium concentration, and its addition to the prepared cells, and finally the measurement of the photoemission.

Furthermore, as mentioned above, light is emitted only during 20 to 30 seconds after activation of the GPCR. Therefore, the recording of the emitted light must be performed during the few seconds following agonist addition to the cells.

Therefore, the methods used in the state of the art are not adequate for a detection based upon high-throughput screening level, which usually need luminometer(s) and require the use of microtiter plates for the testing of thousands of compounds.

AIMS OF THE INVENTION

The present invention aims to provide a method and means, which do not present the drawbacks of the state of the art, for detecting biologically active substances, especially agonists and/or antagonists for calcium-coupled receptors.

A main aim of the present invention is to provide such method and means which allow the detection of biological active substances at a high-throughput scale, which could be adapted to specific recipients such as microtiter plates without requiring the modification of the high-throughput screening device.

Another aim of the present invention is to provide an easy and non-expensive method that could be easily automated.

SUMMARY OF THE INVENTION

The present invention is related to a high-throughput screening diagnostic and/or dosage method of an agonist and/or an antagonist for a "calcium-coupled" receptor, comprising the following successive steps:

- disposing an agonist and/or an antagonist (preferably of a molecule) of said receptor upon a solid support,
- incubating one or more cell(s) expressing apoaequorin and said "calcium-coupled" receptor with coelenterazine in order to reconstitute an active aequorin by said cell(s)
- adding to said solid support one or more of said cells, and obtaining the measurement of an emitted light by said cell(s).

The term "calcium-coupled" receptor means any receptor (such as a G-coupled receptor or an ion channel) whose activation (by an ion, a known or unknown agonist or antagonist molecule) may increase an intracellular calcium; concentration in the cell comprising said receptor, preferably in its cytoplasmic membrane.

The terms "disposing . . . upon a solid support" means the step of putting said compound into a recipient such as a microtiter plate or any other solid support without requiring any (covalent or other) fixing of said compound to said solid support.

Advantageously, the solid support is a microtiter plate, preferably a 96-well microtiter plate.

Advantageously, the cell expressing apoaequorin and the calcium-coupled receptor is a cell expressing a G-coupled receptor and possibly one or more protein(s) intended to ensure a coupling of the receptor to the calcium pathway.

Preferably, said protein is selected from the group consisting of a natural G$\alpha$16 or G$\alpha$15 protein, a chimeric G-protein resulting from a fusion between two different G-proteins or a phospholipase CP2 protein.

The measurement of the emitted light is advantageously obtained with one or several luminometer(s), possibly equipped with several dispensers and measurement heads.

The present invention is also related to a high-throughput screening diagnostic and/or dosage device intended for the diagnostic and/or dosage method according to the invention, said device comprising the following elements:

- a recipient, preferably a microtiter plate, more preferably a 96-well microtiter plate,
- a medium containing cell(s) expressing apoaequorin and a calcium-coupled receptor,
- a medium containing coelenterazine, and
- means (such as one or more luminometer(s) equipped with one or several dispensers and measurement heads) for; detecting and possibly quantifying an emitted light by said cell(s).

Advantageously, the device according to the invention comprises means for the automatic performance of the successive steps of the diagnostic and/or dosage method according to the invention.

A last aspect of the invention is related to the agonist and/or the antagonist of a calcium-coupled receptor identified by the method or the device according to the invention.

The present invention will be described in details in the following non-limiting examples, in reference to the enclosed figures.

DESCRIPTION OF A PREFERRED EMBODIMENT OF THE PRESENT INVENTION

Detection of agonistic activities by means of mammalian cell lines expressing apoaequorin and a GPCR requires the measurement of the emitted light to be performed just after placing the cells in contact with the potential agonist. This can easily be measured at low throughput using a single-tube luminometer. However, up to now, this biological system could not be used at a high-throughput scale. Indeed:

(1) the necessity to measure light just after placing the cells in contact with the agonist to be tested compels to use a luminometer equipped with a build-in dispenser. For example, due to the short duration of light emission, it is impossible to inject the drugs to be tested on the cells placed in the 96 wells while the plate is outside the luminometer and to subsequently record emitted light with the plate into the luminometer. Even if the plate could rapidly (i.e. in less than 15 seconds) be placed into the luminometer after injection of the drugs to be tested, current apparatus do not allow the measurement of light from the 96 wells before the extinction of the flash signal of aequorin, as these luminometers are not equipped with 96 detectors.

(2) luminometers equipped with a build-in dispenser only allow to inject a single solution into the 96 wells, making it impossible to inject a different drug in each well. Moreover, the washing of the dispenser, before each measurement, for the injection of another drug in the next well, is time-consuming and thus is not suitable for the high-throughput scale. The same problem occurs with devices equipped with 6 dispensers (e.g. the "Microbeta Jet" from EG&G Wallac) as the 6 dispensers only deliver a single solution.

The present invention provides a method for performing high-throughput screening of drugs binding to GPCR by the use of mammalian cell lines expressing apoaequorin and a GPCR and by the use of a conventional luminometer. Following this method, the solutions to be tested for (ant) agonistic activities are placed in the wells of a 96-well plate. Cells expressing apoaequorin and a GPCR are detached from the culture plate (or collected from suspension cultures) and are incubated with coelenterazine to reconstitute active aequorin. These are then maintained in suspension with a magnetic stirrer and the cell suspension is injected, well by well, on the solutions of potential agonist to be tested. Light emission is then recorded for 1 (alternatively up to 30 or more) seconds. This method, by injecting the same cell suspension in each of the 96 wells, avoids the need of washing the dispenser between each measurement and allows to perform 96 measurements of agonist-induced aequorin light emission in 15 minutes or less with a single dispenser luminometer. Alternatively, it allows to perform 96 measurements of agonist-induced aequorin light emission in 2 minutes or less with a luminometer equipped with 6 dispensers and measurement heads (e.g. with the "Microbeta Jet" from EG&G Wallac).

This method thus allows to perform high-throughput screening (10 000 samples/day) with mammalian cell lines expressing apoaequorin and a GPCR and by the use of a conventional luminometer. This reduces the screening time and the amount of drugs needed for each measurement.

This system also allows to perform a functional screening with very few (down to 5000 or less) cells per measurement.

The injection of the cells into the wells containing the agonists did not increase the background of the measurement (that could for example have originated from cell breakage, releasing aequorin molecules from the cells into the culture medium, where the calcium concentration would have triggered the emission of light from aequorin). A signal-to-noise ratio above 50 was commonly obtained with this system of cell injection.

The method according to the invention is suitable for performing high-throughput analysis of GPCR or other calcium-coupled-receptor stimulation by known or potential agonists by means of cells expressing the receptor and apoacquorin. These cells may express apoaequorin in the cytoplasm, as described by Sheu et al. (1993) or Button and Brownstein (1993) or may express apoaequorin in the mitochondria, by means of the addition of a mitochondrial targeting sequence to the aequorin, as used by Stables et al. (1997) or in any other part of the cell. These cells may also express proteins intended to ensure coupling of the overexpressed receptor to the calcium pathway. These may be the natural Gα16 or Gα15 proteins (Milligan et al., 1996), chimeric G proteins resulting from a fusion between two different G proteins (Komatsuzaki et al., 1997), phospholipase C-β2 (Park et al., 1992), or any other "universal coupling" proteins once the cells have been prepared and loaded with coelenterazine, they can be used for several hours (at least 9 hours). The load in coelenterazine and the intensity of the light emitted by the cells upon agonist stimulation lasts is stable for this period of time.

EXAMPLES

Example 1

A CHO cell line expressing the chemokine CCR-5 receptor, the Gα16 coupling protein and apoaequorin was, established. Cells were cultivated as a monolayer in HAM's F12 medium containing 10% Foetal bovine serum (FBS). On the day of the experiment, the culture medium was removed and cells were incubated for 5 min at room temperature in PBS-EDTA (phosphate buffered saline solution without calcium, supplemented with 5 mM EDTA). Cells were detached from the culture vessel by shaking the culture plate by hand and by pipetting up and down. Cells were centrifuged and the supernatant was removed to eliminate the EDTA; the pellet was resuspended in HAM's F12 culture medium without FBS and with 0.14 Bovine Serum Albumin. Cells were counted by means of a Thomas cell, were centrifuged again and were resuspended in HAM's F12 culture medium without FBS and with 0.1% Bovine serum Albumin at a concentration of $5.10^6$ cells/ml. Coelenterazine (or a derivative of it, e.g. Coelenterazines f, h, n, cp ox hcp, from Molecular Probes Inc.) at 500 μM in methanol was added to the cell suspension at a final concentration of 5 μM. The cell suspension was then stored in the dark at room temperature for 3 to 5 h, with shaking every 15 to 30 min to maintain the cells in suspension.

Series of dilutions of known ligands were prepared in HAM's F12 culture medium without FBS and with 0.1% Bovine Serum Albumin and 50 μl of each of these solutions were placed in the wells of a 96-well plate. The cell suspension was diluted 5 times with medium HAM's F12 without FBS and with 0.1% Bovine Serum Albumin and was placed in a glass or plastic container protected from light by wrapping it with aluminium foil A magnetic stirring bar was added to the suspension and a magnetic stirrer was used at low speed (1 to 5 rounds per second) to maintain the cells in an homogenous suspension. The magnetic stirring bar was equipped with a ring to avoid crushing the cells, and the subsequent release of aequorin in the culture medium. Alternatively, a culture vessel equipped for culture of cells in suspension may be used.

Figure 1:
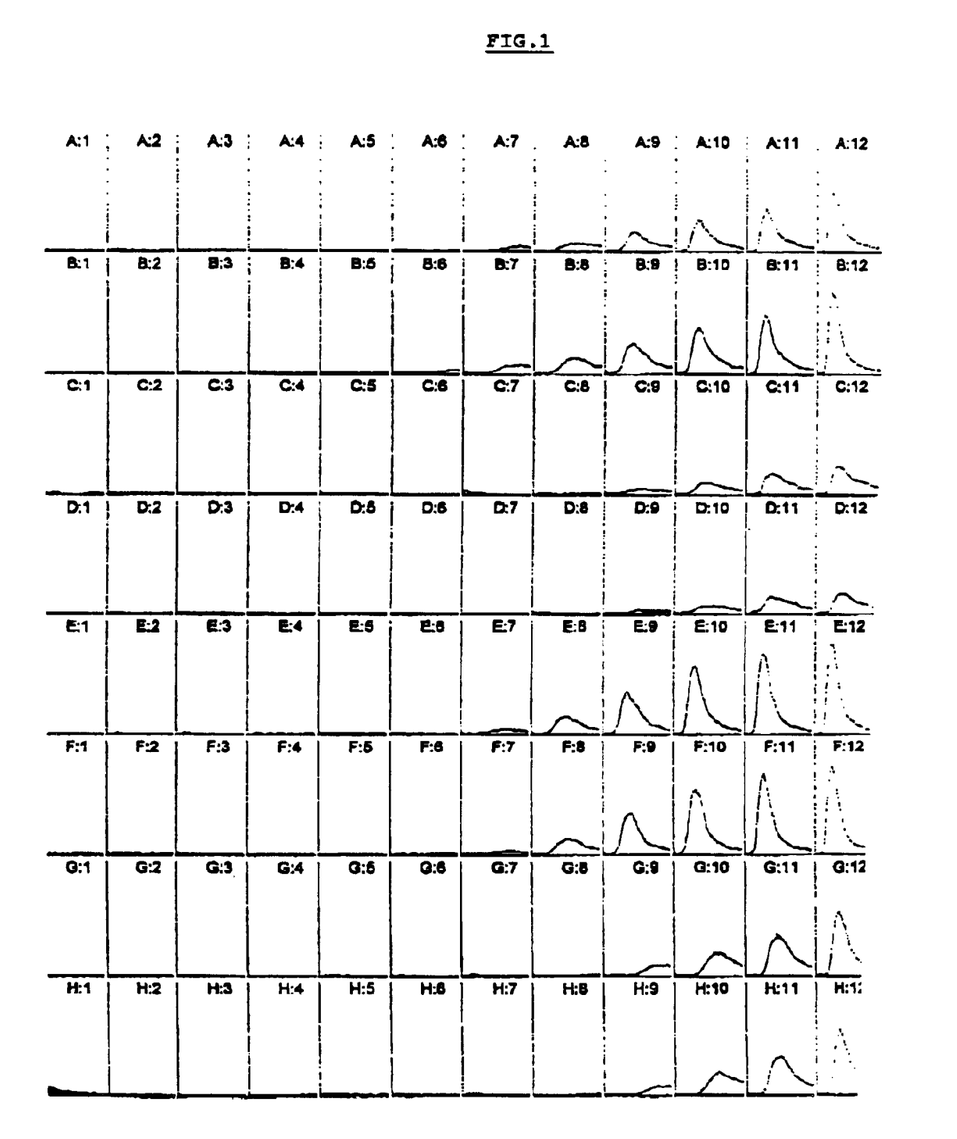
FIG. 1 shows a series curves representing the, intensity of the emitted light by cells as a function of time for each well of a 96-well plate injected with cells expressing the CCR5 receptor, apoaequorin and G$\alpha$16. The scaling is the same for all the graphs. Recording of the signal was performed for 30 seconds. Ligand concentrations are increasing from column 1 towards column 12. All measurements were performed in duplicate: lines A and B: ligand is RANTES; lines C and D; ligand is MIP-1$\alpha$; lines E and F: ligand is MIP-1$\beta$; lines G and H: ligand is derivative A of RANTES.
Figure 2:
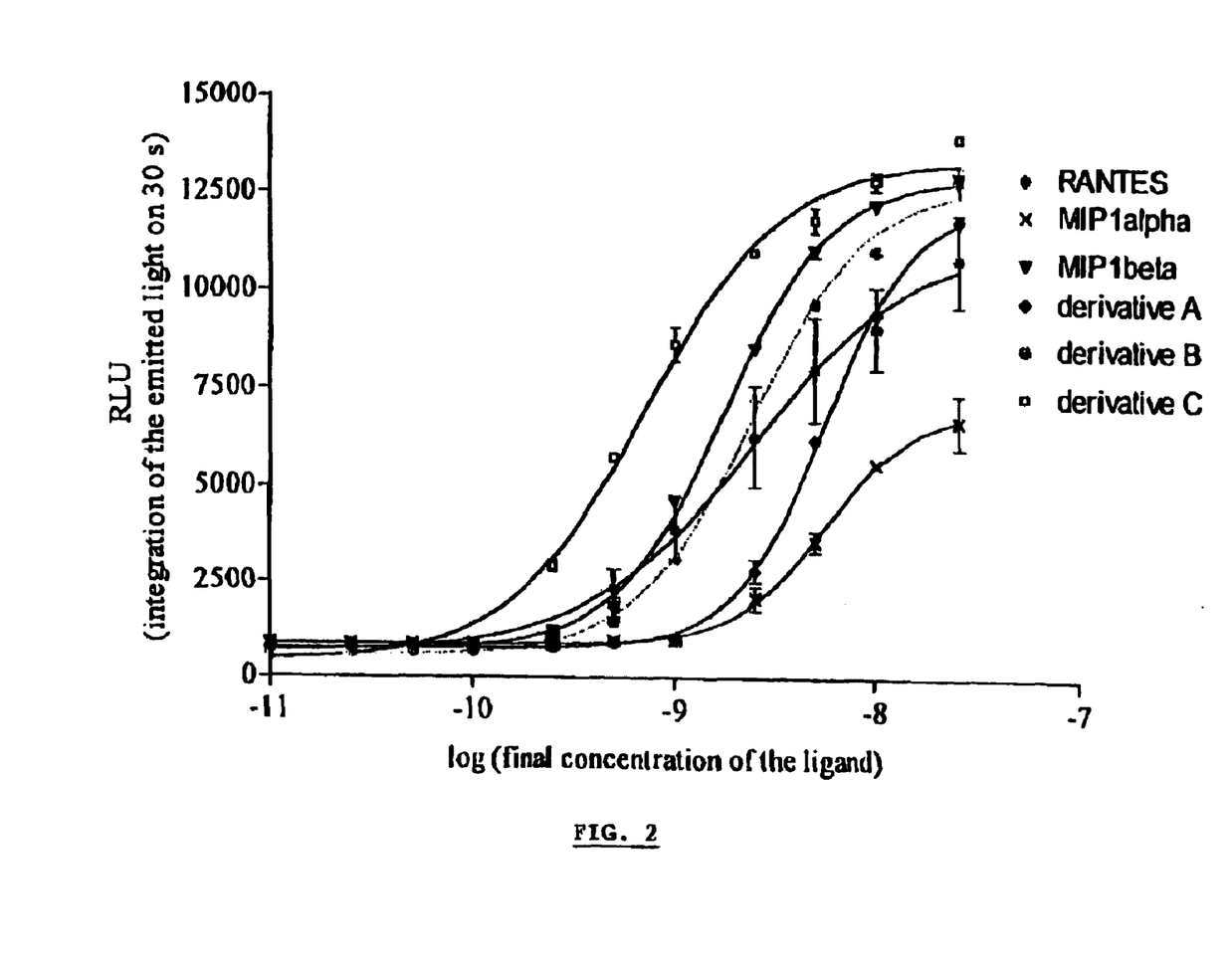
FIG. 2 represents the dose-response curve for different agonists of the CCR5 receptor which represent RLU (integration of emitted light on 30 seconds) according to the logarithm of the final concentration of the ligand.

One uses the EG&G Wallac's MicroLumat-Plus microplate luminometer, which allows injection and direct subsequent recording of the emitted light from each well of a 96-well plate. The end of the entrance tube of the dispenser was placed at the bottom of the cell suspension and the dispenser was washed with 3 times the dead volume of the apparatus so that all the volume of the tube and pumps was filled with the cell suspension. The 96-well plate containing the solutions of agonists was then inserted into the luminometer. Then, for each well, 50 μl of the cell suspension (i.e. 100 000 cells) was dispensed into the well (at the lowest injection speed (0.4 s) to prevent cell breakage that would release aequorin into the culture medium) and the emitted light was immediately recorded during 30 seconds. After reading the first well, cells were injected into the next well and emitted light was recorded, etc. For each plate, a series of curves representing the intensity of the emitted light as a function of time for each well was displayed (FIG. 1). The intensity of the emitted light was integrated over 30 s using the Winglow software provided with the luminometer, yielding for each well one value representative of the emitted light and hence of the stimulation of the CCR-5 receptor by the agonist present in the well. These values can be plotted against the logarithm of the ligand concentration to generate dose-response curve an shown in FIG. 2. These allow the determination of half-maximal response doses ($EC_{50}$) for each ligand. For the generation of these data, 288 measurements were performed in less than 3 hours.

Example 2

Figure 3:
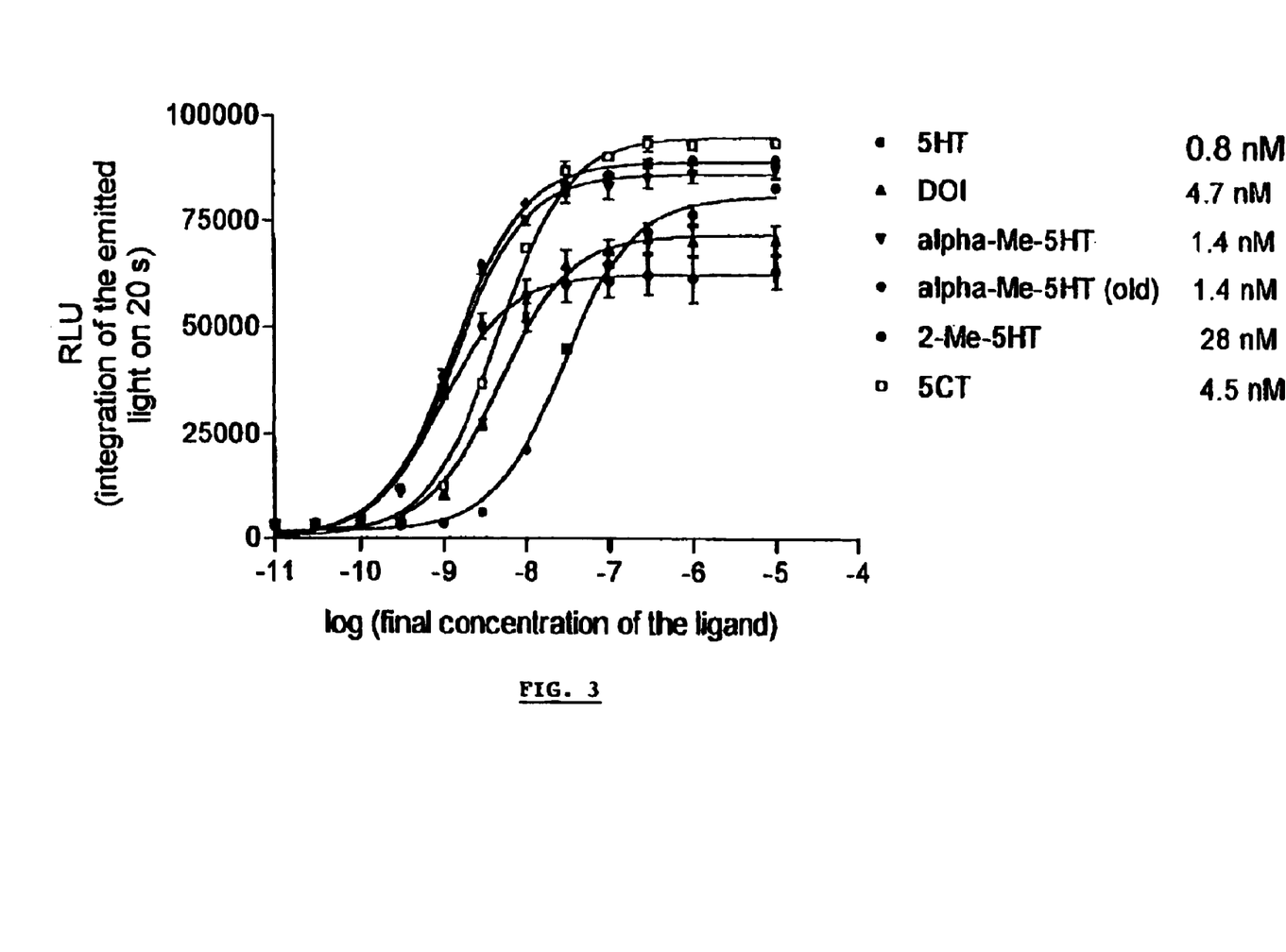
FIG. 3 represents the dose-response curve for different agonist of the 5HT-2B receptor.

A CHO cell line expressing the serotonin 5HT-2B receptor, the Gα16 coupling protein and apoaequorin was established. Cells were treated as described in Example 1 and were dispensed after dilution (100 μl/well, corresponding to 50 000 cells) on 100 μl of solutions of known agonists for this receptor. The emitted light was recorded during 20 s for each well. Dose-response curves obtained for different agonists are shown in FIG. 3. For the generation of these data; 144 measurements were performed in less than 1 hour.

Example 3

Figure 4:
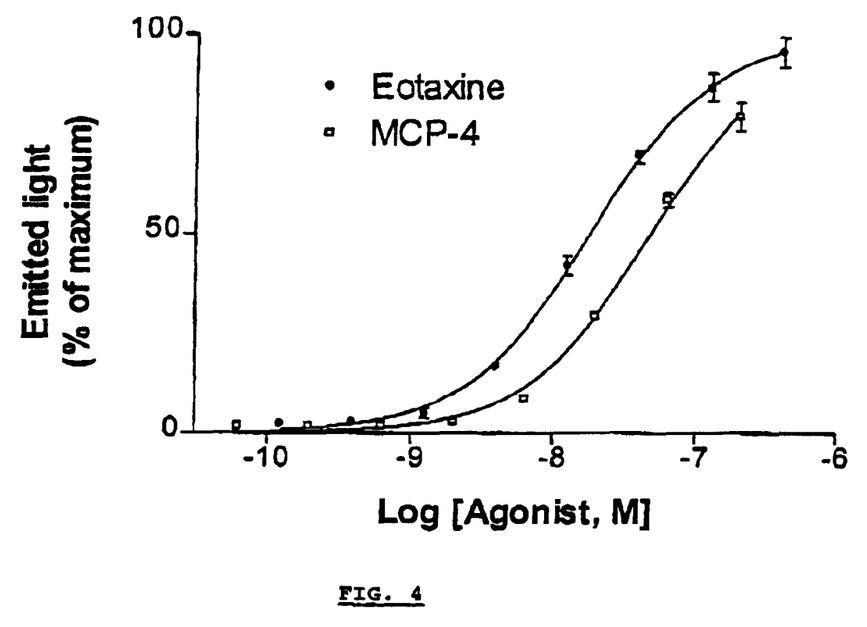
FIG. 4 represents the dose-response curve of the light emitted from K562 cells expressing CCR3 and aequorin as a response to the activation of the receptor by eotaxin.

K562 cells expressing the chemokine CCR3 receptor were transfected by a plasmid for the expression of aequorin and the Gα16 coupling protein. Cells stably transfected were selected for 2 weeks with the antibiotic Zeocin. These cells were cultured in suspension in DM culture medium containing 104 FBS. They were centrifuged and the pellet was used as described in example 1 to perform aequorin measurements. A dose-response curve with eotaxin and MCP-4 generated by this method in described in FIG. 4.

Example 4

Figure 5A:
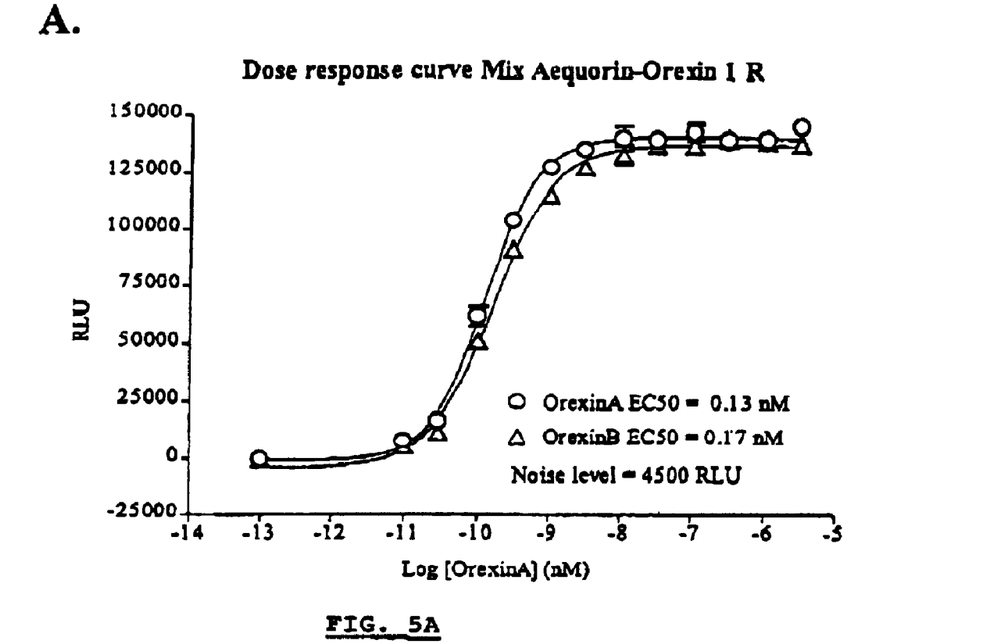
FIG. 5 represents the dose-response curves for cells expressing aequorin and G$\alpha$16 and (panel A) the orexin 1 receptor or (panel B) the orexin 2 receptor.

A CHO cell line expressing the orexin 1 or orexin 2 receptor, the Gα16 coupling protein and apoaequorin was established. Cells were treated as described in Example 1 and were dispensed after dilution (100 μl/well, corresponding to 25 000 cello) on 50 μl of solutions of known agonists for these receptor. The emitted light was recorded during 20 s for each well. A dose-response curve obtained with this method is showed in FIG. 5A.

Example 5

Figure 5B:
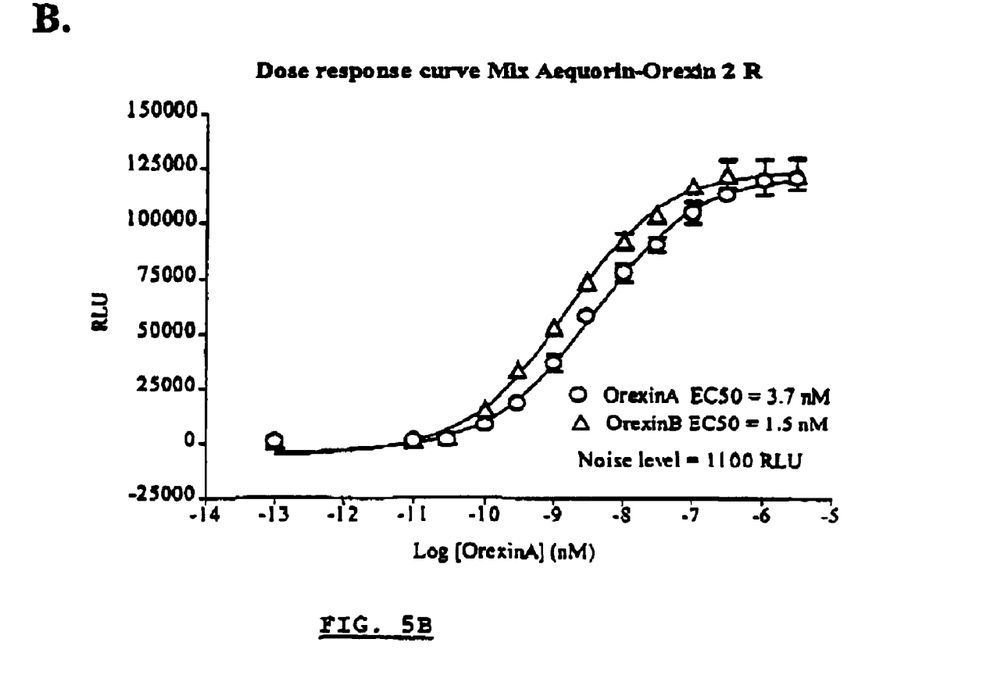

A CHO cell line expressing the canabinoid CB1 receptor, the Gα16 coupling protein and apoaequorin was established. Cells were treated as described in Example 1 and were dispensed after dilution (100 µl/well, corresponding to 50 000 cells) on 100 µl of solutions of a known agonist for this receptor. The emitted light was recorded during 20 s for each well. A dose-response curve obtained with this method is showed in FIG. 5B.

Figure 6:
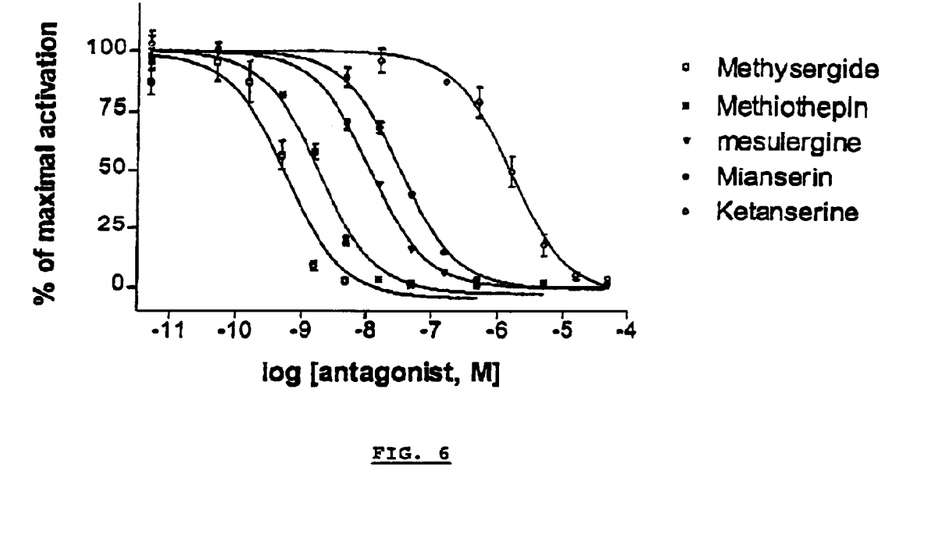
FIG. 6 represents the dose-response curve for different antagonists of the 5HT-2B receptor.

For the measure of antagonistic activities, cells were injected on series of dilutions of antagonists. At this stage, the emitted light was recorded to check that the potential antagonists had no agonistic activity. The cells were incubated with the antagonists for 30 min. A solution of agonist (alpha-methyl-5HT) of the 5HT-2B receptor was then injected on the cells and the emitted light was immediately recorded for each well. The emitted light was plotted as a function of the logarithm of the antagonist concentration to yield the graph shown. Increasing antagonist concentrations result in a decreasing light emission upon agonist addition. An agonist of another receptor expressed by the cells (usually ATP, acting at P2 receptors) can then be injected on the mixture of antagonist, cells and agonists as a control to check that the cells still have active aequorin up to that moment of the experiment. For example, cytotoxic compounds that increase the intracellular calcium concentration can make the aequorin consume all the coelenterazine present in the cell. Such a cytotoxic compound will be detected by the absence of signal upon ATP injection (FIG. 6).

REFERENCES

Button, D. & Brownstein, M., *Cell Calcium* 14, pp. 663–671 (1993)
Komatsuzaki, K. at al., *FEBS Lett.* 406, pp. 165–170 (1997)
Milligan, G. et al., TIPS 17, pp. 235–237 (1996)
Park, D. et al, *J. Biol. Chem.* 267, pp. 16048–16055 (1992).
Rink, T. J., *FEBS Lett.* 268, pp. 381–385 (1990)
Santella, L. & Carafoli, *FASEB J.* 11, pp. 1091–1109 (1997)
Sheu, Y. A. et al, *Analytical Biochemistry* 209, pp. 343–347 (1993)
Stables, J. et al., *Analytical Biochemistry* 252, pp. 115–126 (1997)
Tsunoda, Y., *Biochim. Biophys. Acta* 1154, pp. 105–156 (1993).

What is claimed:

1. A method for the identification of an agonist, antagonist or any modulator of a calcium-coupled receptor, comprising:
    (a)—disposing a compound on a solid support,
    (b)—incubating one or more cell(s) expressing apoaequorin and said calcium-coupled receptor with coelenterazine in order to reconstitute an active aequorin by said cell(s),
    (c)—adding one or more of said cells to said solid support with said compound, and
    (d)—measuring the light emitted by said cell(s).
2. The method according to claim 1, wherein the solid support is a microtiter plate.
3. The method according to claim 2, wherein said microtiter plate is selected from the group consisting of: a 96-well microtiter plate, a 384-well plate, and a 1536-well plate.
4. The method according to claim 1, wherein the cell expresses apoaequorin in the cytoplasm or in the mitochondria.
5. The method according to claim 1, wherein the cell expressing said calcium-coupled receptor is a cell expressing an endogenous or a recombinant G-protein-coupled receptor and/or a cell which expresses a protein intended to ensure a coupling of the analysed receptor to the calcium pathway.
6. The method according to claim 5, wherein said G-protein or said protein intended to ensure a coupling of the analysed receptor to the calcium pathway is selected from the soup consisting of: natural Gα16 or Gα15 protein, chimeric G-protein resulting from a fusion between two different G-proteins, and a phospholipase Cβ2 protein.
7. The method according to claim 1, wherein the measurement of the emitted light is obtained with one or more luminometer(s) equipped with several dispensers and measurement heads.
8. The method of claim 1, wherein said calcium-coupled receptor is a calcium coupled ion channel.

* * * * *

UNITED STATES PATENT AND TRADEMARK OFFICE
CERTIFICATE OF CORRECTION

PATENT NO. : 6,872,538 B1
DATED : March 29, 2005
INVENTOR(S) : Dupriez et al.

It is certified that error appears in the above-identified patent and that said Letters Patent is hereby corrected as shown below:

Column 8,
Line 29, claim 6 should read,
6. The method according to claim 5, wherein said G-protein or said protein intended to ensure a coupling of the analysed receptor to the calcium pathway is selected from the group consisting of: natural Gα16 or Gα15 protein, chimeric G-protein resulting from a fusion between two different G-proteins, and a phospholipase Cβ2 protein.

Signed and Sealed this

Thirty-first Day of May, 2005

JON W. DUDAS
*Director of the United States Patent and Trademark Office*